United States Patent [19]

Muriot

[11] 4,004,590
[45] Jan. 25, 1977

[54] MEDICAL/SURGICAL SUCTION EQUIPMENT

[75] Inventor: Edward E. Muriot, Horsham, Pa.

[73] Assignee: Health Technology Laboratories, Inc., Horsham, Pa.

[22] Filed: Dec. 3, 1975

[21] Appl. No.: 637,140

Related U.S. Application Data

[63] Continuation-in-part of Ser. Nos. 524,052, Nov. 15, 1974, and Ser. No. 614,226, Sept. 17, 1975, which is a continuation of Ser. No. 497,838, Aug. 16, 1974, abandoned.

[52] U.S. Cl. .............................................. 128/276
[51] Int. Cl.² ...................................... A61M 1/00
[58] Field of Search ................... 128/276–278, 128/297–300, DIG. 12, DIG. 24, 214 D, 214 F; 277/178; 220/9, DIG. 9; 312/296; 285/192; 141/59; 27/24 R

[56] References Cited

UNITED STATES PATENTS

| | | |
|---|---|---|
| 2,757,669 | 8/1956 | Gewecke et al. ........... 128/DIG. 12 |
| 3,032,037 | 5/1962 | Huber ............................... 128/276 |
| 3,142,298 | 3/1964 | Koski et al. ...................... 128/276 |
| 3,640,276 | 2/1972 | Dancy et al. .................. 128/214 F |
| 3,722,557 | 3/1973 | Huggins ......................... 128/214 D |

*Primary Examiner*—Robert W. Michell
*Assistant Examiner*—Henry S. Layton
*Attorney, Agent, or Firm*—Synnestvedt & Lechner

[57] ABSTRACT

Equipment for medical or surgical uses is provided for purposes, for example, of withdrawing or draining body liquids from cavities tending to accumulate such liquids, for instance as a result of wounds, surgical procedures or of pathological conditions in the body. The equipment comprises a vacuum chamber having a wall structure and a door cooperating to provide a closed but openable vacuum compartment adapted to receive a disposable collection bag. The bag has a liquid inlet tube and the wall structure and door have portions cooperating to form a channel therebetween for receiving the inlet tube, and the inlet tube carries a sealing device insertable into and removable from said channel with the tube in a direction transversely of the tube when the door is open.

9 Claims, 18 Drawing Figures

MEDICAL/SURGICAL SUCTION EQUIPMENT

This application is a Continuation-in-part of my application Ser. No. 524,052, filed Nov. 15, 1974 and also of my application Ser. No. 614,226, filed Sept. 17, 1975, which latter application is a continuation of my application Ser. No. 497,838, filed Aug. 16, 1974 now abandoned.

The present invention relates to suction equipment for use for medical or surgical purposes, and particularly to accumulate in cavities or regions of the body because of disease or malfunction or other pathological conditions, or because of surgical or medical procedures. Such conditions at times may also tend to accumulate solids, and it will be understood that the equipment of the invention may also serve to withdraw such solids in suspension in liquids being withdrawn.

As brought out in my copending applications above referred to, the equipment there disclosed is arranged to function on the vacuum or suction principle, without the flow of the liquids through a mechanical pump or pumping mechanism, as has been the case in certain prior arrangements.

Provision is also made for a high degree of flexibility in the control of the suction, both with respect to the amount of suction applied, and also with respect to the timing thereof. Thus, provision is made not only for adjustment of the amount of vacuum or suction, but also for alternative conditions of operation in which the suction may either be applied continuously, or may be applied intermittently, or may be applied in a manner providing intermittent fluctuation of the suction between high and low suction values.

In accordance with another aspect of the invention, the equipment includes a vacuum chamber having a vacuum line connected therewith, the chamber being adapted to receive a disposable suction bag. According to the invention the chamber has a wall structure with an opening or doorway, and a door is provided, the wall structure and door having portions forming a channel therebetween providing for transverse insertion and removal of the intake tubes of the disposable suction bags employed, and thereby eliminating the necessity for longitudinal threading of a tube through a port or aperture in the chamber wall.

It is also an object of the invention to provide alternatively for insertion of one or more than one bag in the vacuum chamber, each such bag having an intake tube with a catheter for receiving liquids either from the same or from different sources.

It is an object of the invention to provide an exceedingly simple and effective system for replacing the disposable bag and catheter, notwithstanding the enclosure thereof in the vacuum chamber during use of the equipment.

It is another object of the invention to provide sealing means for the intake tube of the bag at the point where the tube extends through the channel formed between the wall of the vacuum chamber and the door, and it is contemplated according to the invention that sealing means or devices be provided to accommodate intake tubes of different sizes.

Still another object of the invention is to provide sealing means, of the kind just referred to, in the form of an adaptor which is preferably permanently fastened to the intake tube, thereby avoiding inadvertent use of adaptors of the wrong size by personnel operating the equipment.

The invention also contemplates provision of a bag with a connected intake tube carrying sealing means, arranged as a disposable unit unitarily separable from the chamber and its door independently of the vacuum line for the chamber.

The foregoing provisions eliminate sterilization and cross contamination problems, as will further appear.

How the foregoing and other objects and advantages are attained will appear more fully from the following description referring to the accompanying drawings, in which:

FIGS. 14 to 18 inclusive illustrate another embodiment of sealing arrangements for the vacuum compartment and for the suction tube for the bag, this embodiment being adapted for use in either of the embodiments of the equipment as shown in FIGS. 1–4 and 5–6, the individual figures of this group representing parts of the equipment as follows:

Reference is first made to the overall general configuration of the equipment shown in FIGS. 1–4. It will be seen that the vacuum chamber of this embodiment is made up of assembled flat sheets or wall elements, at least some of which are preferably formed of plastic or resin material such as polymethyl methacrylate. The vacuum chamber is defined by a back wall 50, top and bottom walls 51 and 52, upright end walls 53, and an inclined front wall 54. At least the front wall 54, which is arranged to serve as a door or closure, as more fully brought out herebelow, is preferably formed of transparent material, and desirably also the side walls. The vacuum chamber is arranged above a cabinet or base 55 adapted to enclose certain operating parts, as will further appear, this base desirably being substantially completely enclosed, except for certain ports or passages through which connections extend, as will be described. Below the bottom wall of the base or enclosure 55 means for supporting the unit are provided, preferably including a pair of laterally spaced wheels 56, and a pair of downwardly projecting spaced side wall elements 57, which may conveniently take the form of triangular pieces, with one corner of each presented downwardly to provide for support as on the floor indicated at F in FIG. 1.

With the equipment arranged in the general manner described above, the various components are conveniently arranged and assembled in an overall structure which may readily be wheeled from place to place and which will also stand in a stable upright position because of the supporting elements 56 and 57.

With regard to the general arrangement it is further to be observed that superimposed above the top wall 51 of the vacuum chamber a control box is provided as indicated at 58, this box having a top wall or panel 59 with which various of the operating controls are associated, especially those which are located within the control box 58.

Figures 1, 2, 3:
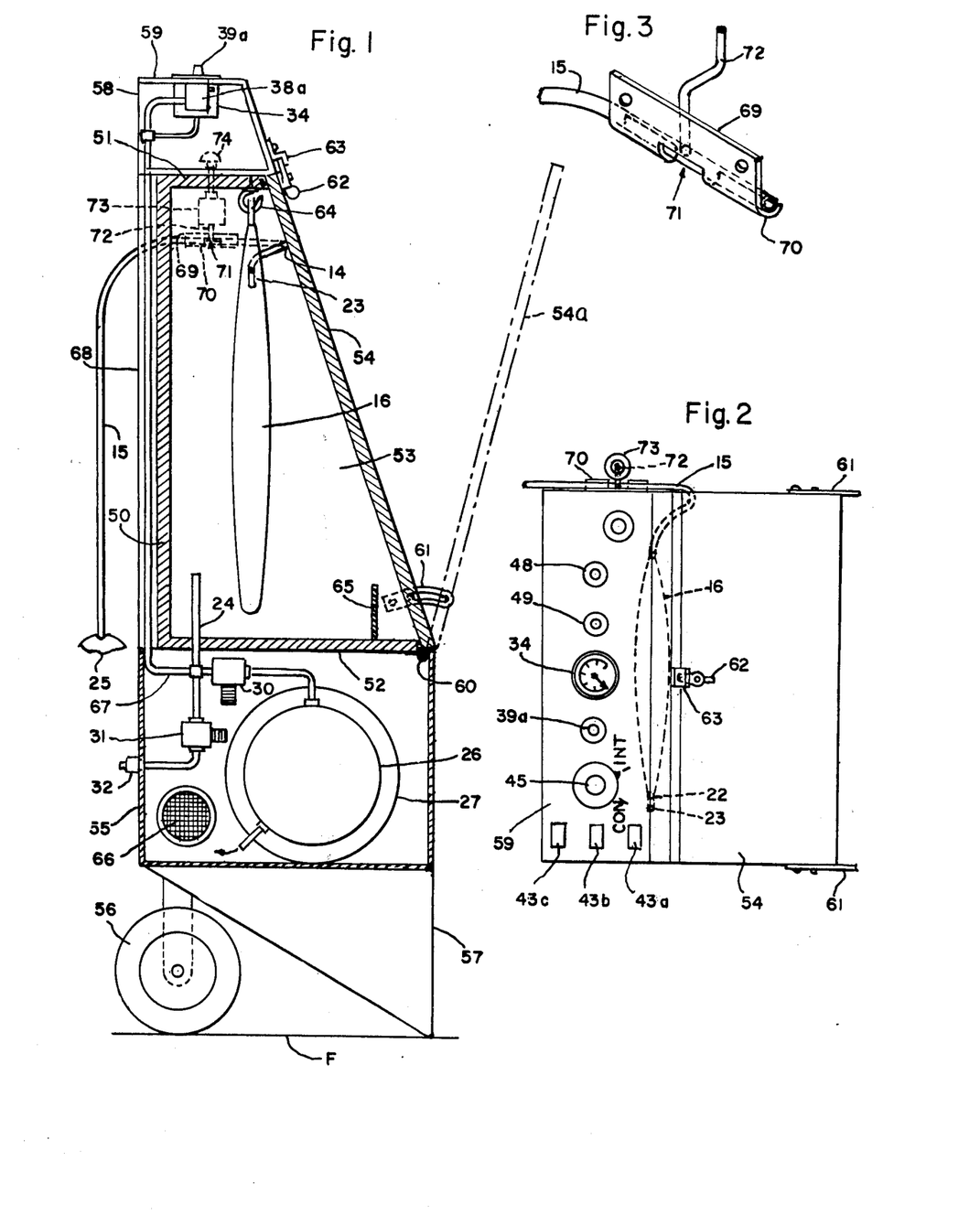
FIG. 1 is a vertical sectional view of one embodiment of the suction equipment according to the present invention.
FIG. 2 is a plan view of the equipment shown in FIG. 1.
FIG. 3 is an enlarged isometric fragmentary view of one form of device used for establishing intermittent operation in the embodiment of FIGS. 1 and 2.

The inclined front wall 54 is preferably hinged along its lower edge as indicated at 60 so that this wall serves as a displaceable closure or door movable between the full line closed position shown in FIG. 1 at 54 and the dot-dash open position 54a. Straps 61 each having a slot cooperating with a pin are provided to limit the opening movement of the front wall in the manner plainly shown in FIG. 1. The wall 54 may be fastened in closed position by means of a pivoted latch device 62 cooperating with a keeper 63.

Opening the front panel provides for ready access to the suction bag indicated at 16, which is conveniently hung from hooks 64 depending from the top wall 51 of the vacuum chamber.

A disposable suction bag 16 is employed having an intake tube 15 desirably constituting a disposable unit. These parts are desirably formed of flexible plastic material, preferably transparent or at least translucent so that the quantity of liquid in the bag may be observed and the bag may have a series of graduations from which a reading may be taken of the volume of liquids contained in the bag. The tube may be connected with the bag, for instance by use of an attachment nipple as described hereinafter with reference to FIG. 14.

The suction tube 15 may terminate in or be provided with a disposable catheter for insertion into the zone or body cavity from which the liquids are to be withdrawn. The bag also has a drain spout or outlet tube 22 with a cap 23 connected with the bag in an upper portion thereof above the normal level to which the bag is filled. The details of construction of the spout and cap appear in FIGS. 12 and 13. Tube 22 has a longitudinal rib 22a, so that when the cap 23 is applied there remain small leakage passages at each side of the rib 22a. This provides for communication of the vacuum in the chamber into the interior of the bag, so that the actual transfer of the liquids is effected under the influence of atmospheric or other pressure upon the liquids in the region of the catheter, which pressure, and the reduced pressure established in the bag by the vacuum provides the pressure differential which is effective to transfer the liquids from the zone being drained into the bag. A wad of cotton or other similar material 23a in the cap 23 acts as a filter preventing transfer of liquid or contaminants from the bag into the surrounding vacuum chamber. If desired the cap may be removed to permit use of the spout 22 as a drainage tube for emptying the bag, for purposes of analysis, test or disposal.

The bag may be supported within the vacuum chamber by various supporting devices preferably cooperating with the top portion of the bag, as by hooks 64 depending from the top wall 51 of the vacuum chamber. With the bag suspended at the top as just described and with the closure 54 displaced outwardly about the hinge 60, and still further with the notch 14 in the edge of the side wall of the vacuum chamber for receiving the tube 15, the insertion and replacement of the disposable bags is exceedingly simple and may be effected with minimum effort and time.

The suspension of the bag at the top, as shown, and the connection of the suction tube 15 with the upper region of the bag is also advantageous because this arrangement avoids interference with or alteration of the suction as a result of build up of the body of liquid within the bag. If the suction tube 15 were connected with the bottom or in the bottom region of the bag, the gravity head of the accumulating liquid would interfere with and reduce the suction action, and this is avoided by arranging the suction connection so that it communicates with the suction bag in the upper portion thereof, and in any event above the level to which it is intended that the liquid would be permitted to rise in the bag.

It is to be understood that sealing gaskets or other sealing elements as described hereinafter are employed to avoid leakage and loss of vacuum, for instance along the meeting edges of the displaceable wall 54 and the side, top and bottom walls of the chamber, as well as in the region of the notch 14 for accommodation of the suction tube 15.

In the bottom portion of the suction chamber an upright wall 65 is provided, projecting upwardly from the bottom wall 52 and extending laterally between the side walls 53, this wall 65, cooperating with other wall elements of the vacuum chamber to define a sump which will receive and retain liquids, in the event of inadvertent spillage or leakage, for instance because of a damaged suction bag. Preferably the wall 65 is of sufficient vertical height so that the sump provided has a volumetric capacity at least as great as the normal charge in one of the suction bags. It will also be noted that the vacuum connection 24 which extends upwardly through the bottom wall of the vacuum chamber extends to a height somewhat above the upper edge of the wall 65, so that even in the event of accumulation of liquid in the sump, this liquid will not enter the vacuum system.

It is contemplated that the equipment shown in FIGS. 1–4 be capable of operation either by the action of a self-contained aspirator comprising the suction pump 26 and motor or by an externally available vacuum source which may be coupled with the equipment by means of the plug-in vacuum connection 33, cooperating with the connector 32.

The first of these two sources of vacuum (the pump 26) is coupled with the connection 24 through a normally closed solenoid operated valve 30. The second of these two sources is adapted to be coupled with the vacuum connection 24 through another normally closed solenoid operated valve 31 which, in turn, is connected with the coupler 32 provided in the wall of the base 55. A removable length of tubing 33 having separable couplers at both ends serves to connect the vacuum wall outlet commonly provided in hospital rooms with the coupling 32, and thereby provide for completion of the flow path from the vacuum connection 24 to the standard vacuum wall outlet.

A pressure gauge 34 is associated with the connection 24 in order to provide a reading of the pressure level or vacuum established within the vacuum chamber.

Thus, in this embodiment, these two sources of vacuum are respectively controlled by normally closed solenoid operated valves 30 and 31, both of these valves being associated with the vacuum connection 24 which is extended from the base enclosure upwardly into the vacuum chamber independently of the suction bag and its intake tube. Preferably the base enclosure 55 is provided with an opening with which a filter device 66 is associated, desirably in the form of a replaceable filter unit, so that any discharge through the opening from the interior of the base enclosure from the suction pump 26 will be filtered before discharge into the surrounding air.

Figure 4:
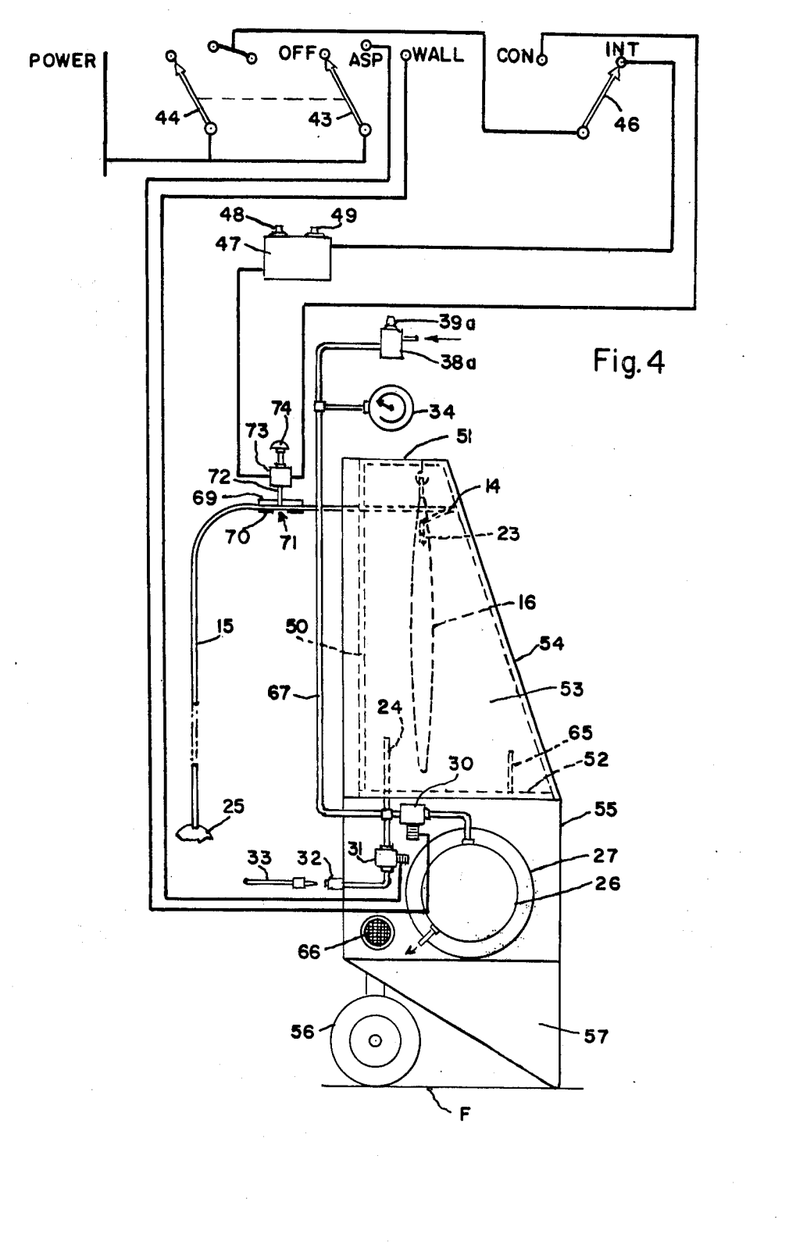
FIG. 4 is a schematic view of the fluid pressure and other controls employed with the equipment of FIGS. 1, 2 and 3.

The arrangement of the controls appears to best advantage in the schematic view of FIG. 4. Here it will be seen that the vacuum connection 24 which communicates with the intake sides of the solenoid valves 30 and 31, also communicates with a connection 67 which extends from the base enclosure upwardly at the back of the vacuum chamber, for instance through an enclosed duct or channel 68 (see especially FIG. 1), this connection 67 being associated with controls arranged in the control box 58 at the top of the unit, as described below with particular reference to the schematic view of FIG. 4.

A pressure gauge 34 is associated with the vacuum line 67, and in addition an adjustable bleed valve 38a, having an adjustable control knob 39a is associated with the vacuum connection 67, these devices (34 and 39a) being mounted on the panel 59 at the top of the control box, as will be seen from FIG. 2. A timer device 47 is also located in this control box and the two control knobs 48 and 49 of this timer are positioned above the panel 59 as also appears in FIG. 2.

The timer mechanism in the embodiment of FIGS. 1 to 4 is arranged to operate on the suction tube 15 which, in effect, is the pressure side of the system, i.e., the side at which atmospheric pressure is acting to cause flow of the liquids through the tube 15 into the suction bag. Outside of the vacuum chamber, at one side wall thereof, a bracket 69 is provided, the lower edge of this bracket having an upwardly open channel 70 adapted to receive the tube 15. When a bag is inserted in the vacuum chamber and the tube introduced into the notch 14, the tube may also be manually laid into the channel 70 and then extended to the source 25 of the liquid to be drawn into the suction bag. The midportion of the channel 70 is cut away as indicated at 71 in FIG. 3, in a position below the plunger 72 of the solenoid device 73. The solenoid device is of the type in which the plunger 72 is biased downwardly, as by spring pressure, and when the plunger is pressed downwardly against a tube 15 in the channel 70, the tube will be closed be being deflected into the recess 71. The plunger 72 may be manually lifted by the handle 74 provided at the top of the solenoid device. The plunger 72 may also be raised by action of the solenoid under the influence of the timer 47, in which event the raising of the plunger will be intermittent, the control knobs 48 and 49 providing for control of the period during which the plunger is raised and also for control of the interval between periods when the plunger is raised.

The solenoid 73 may be activated constantly, thus maintaining the plunger 72 in raised position at anytime the switch 46 is positioned in the CON (continuous) position.

The arrangement of FIGS. 1-4 includes a control knob 45 for the switch providing for alternative intermittent or constant operation (see FIG. 2). In addition switch buttons 43a, 43b and 43c are provided on the control panel as shown in FIG. 2, these buttons serving to operate the switch parts indicated at 43 and 44 in FIG. 4 and serving respectively to establish the OFF, ASP (self-contained "aspirator") and WALL (external vacuum) conditions.

The arrangement of the solenoid 73 as described hereinabove, has a number of distinctive advantages including the fact that at anytime when the system is completely turned off, as by pushing the OFF button, the plunger 72 will close the tube 15, which is desirable in order to prevent gravity flow of liquid in reverse direction through the tube 15 to the body cavity from which liquids have been withdrawn.

When the equipment is being operated with the switch 46 in the CON position the plunger 72 will be lifted so that fluids may be drawn through the tube 15 into the suction bag 16. When the switch 46 is in the INT (intermittent) position the plunger 72 will be intermittently raised and lowered, thereby intermittently opening and closing the suction tube 15. This provides an intermittent suction operation without changing the vacuum or pressure reduction in the vacuum chamber and the suction bag. This provides for intermittent operation without involving any time delays for pressure reduction or pressure increase in the vacuum chamber. The positioning of the tube 15 in the channel 70 is a simple and readily effected operation, merely requiring manual lifting of the spring pressed plunger 72 by the handle 74, in order to raise the plunger to a position above that established by the solenoid and its return spring, so that the tube may readily be placed in the channel 70 below the plunger 72. Upon release of the handle the plunger will descend under the action of the return spring to close the tube, unless the equipment is in operation, in which event the plunger will be kept by the control circuits in the position shown in which the tube is open.

Figure 5:
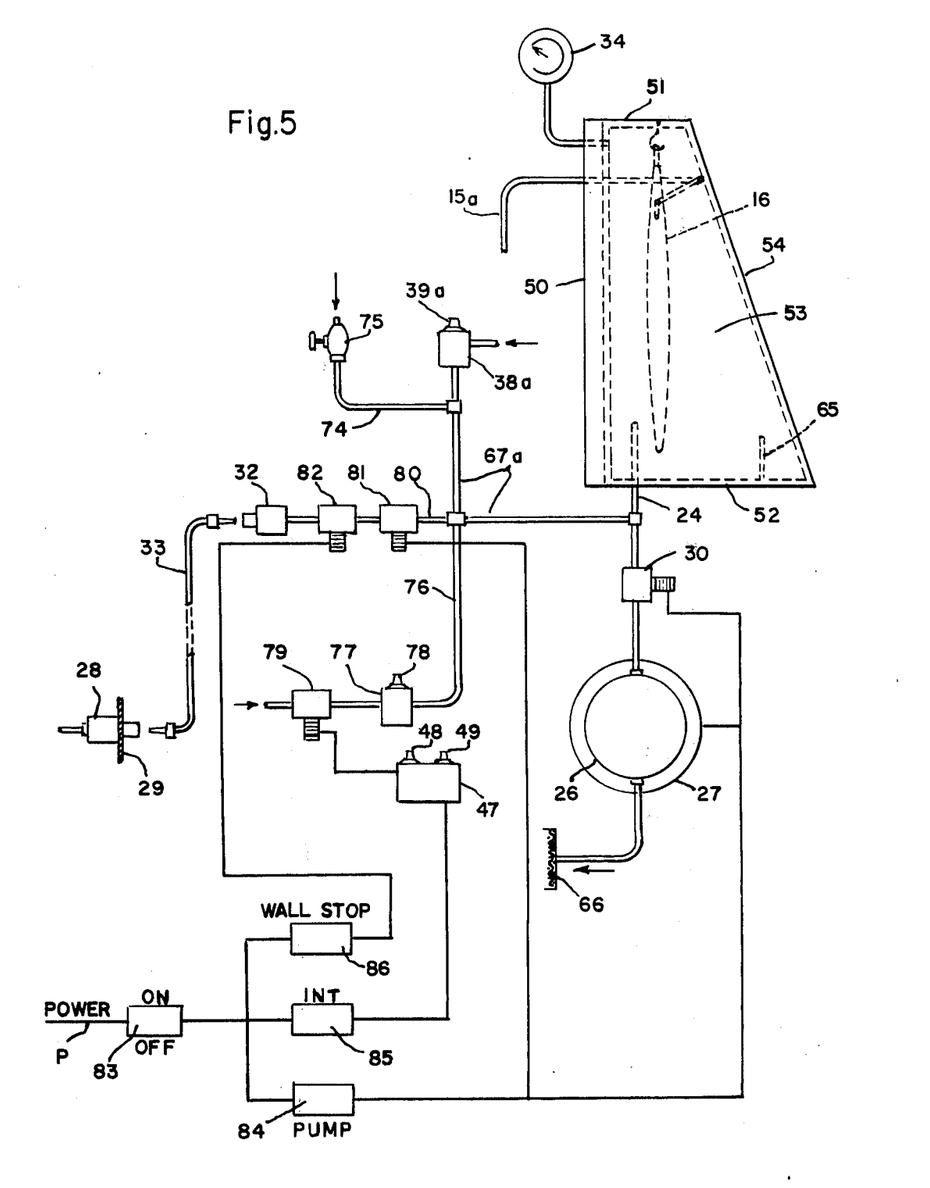
FIG. 5 is a schematic view of the general type of FIG. 4 but illustrating certain parts of a second embodiment of the equipment and controls.
Figure 6:
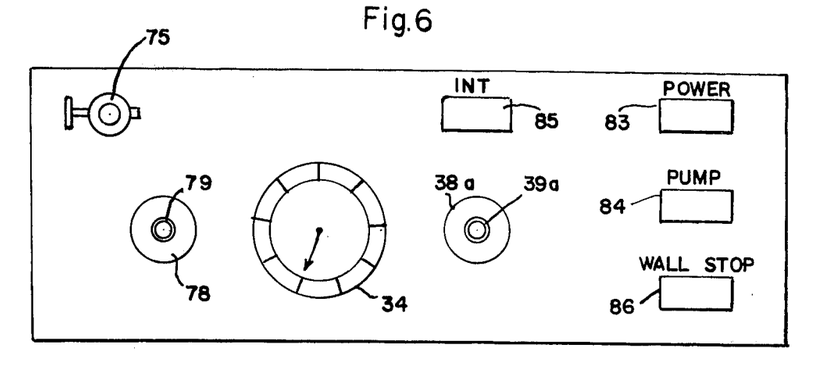
FIG. 6 is a view of a control panel contemplated for use with the controls shown in FIG. 5.

Turning now to the embodiment of the equipment as illustrated in FIGS. 5 and 6, it is first to be understood that although not all parts of the equipment are shown in these figures, the parts which are not illustrated may be of the kind disclosed above, in the embodiment which is shown in FIGS. 1 to 4, but the equipment of the second embodiment incorporates certain differences as compared with the equipment of the first embodiment as will be pointed out.

It is also to be understood that certain of the features described herebelow in connection with the second embodiment may also be used in the first embodiment, for instance the phases of the control system providing for automatic change over of operation from the self-contained suction source to an external suction source, and also the sealing means for the suction tube, as particularly described with reference to FIGS. 7 to 11.

Still further it is to be understood that bags and suction tubes of the kind described above are contemplated for use also in the second embodiment.

Figures 12, 13, 14, 15, 16:
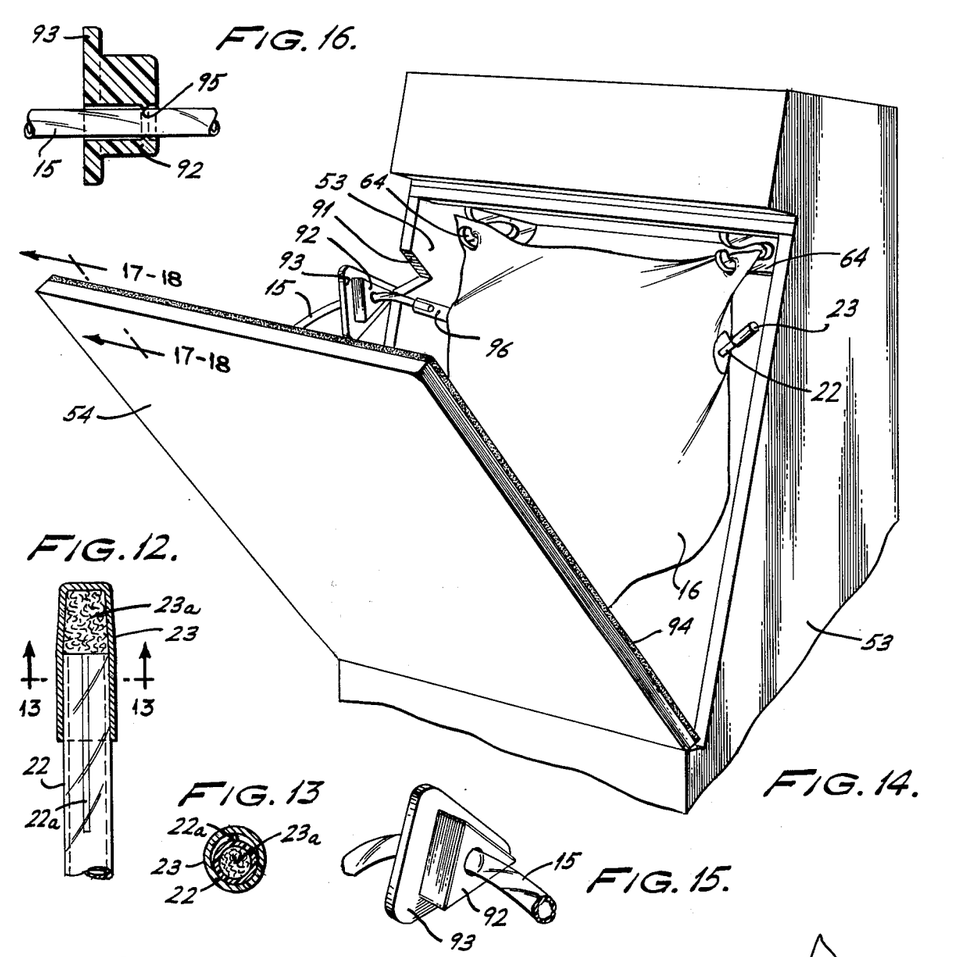
FIG. 12 is an axial sectional view of the outlet tube of the bag employed.
FIG. 13 is a cross sectional view taken as indicated by the line 13—13 on FIG. 12.
FIG. 14 is a perspective view of the vacuum compartment with the door shown in open position, and illustrating a bag suspended in the compartment, the bag having a suction tube with a modified form of tube seal associated therewith.
FIG. 15 is an enlarged detailed perspective view of the suction tube and sealing device of this embodiment.
FIG. 16 is a sectional view through the sealing device taken in the plane of the tube axis.

Turning now to the system as diagramed in FIG. 5, it will be noted that the vacuum chamber of this embodiment is of the kind shown in FIGS. 1 and 4, but in FIG. 5 the mounting of various of the control parts in the base has not been illustrated as this portion of the equipment may be arranged in the same general manner as in the embodiment of FIGS. 1–4. The bag in the suction compartment is again indicated at 16 and it is contemplated that this may be the same kind of bag described above, having provision for communication between the interior of the bag and the interior of the chamber as illustrated in FIGS. 12 and 13 and having a suction tube which is here indicated at 15a, which may have certain differences from the tube 15 of the first embodiment, as will be explained hereinafter.

The vacuum system for the vacuum chamber includes the principal vacuum connection 24, of the kind described above, associated with a different form of control system as is illustrated in FIG. 5 and described below.

It is first noted that the pressure gauge 34 is here shown as being directly connected with the vacuum chamber separately from the connection 24, although it will be understood that the pressure gauge may alternatively be connected with the vacuum connection 24.

The self-contained source of suction, namely the motor 27 and the pump 26, is provided and this pump is connectable with the vacuum connection 24 through the solenoid value 30 which is a normally closed value, as in the other embodiment. The discharge of the pump 26 may be delivered through a filter 66, in the manner previously described in reference to FIG. 7.

Connections 67a extend from the main suction line 24 to the adjustable bleed valve 38a, by means of which air may be bled into the system, thereby limiting the maximum suction, in the manner previously described. This device is adjustable by means of the nob 39a. In the embodiment of FIG. 5, a branch connection 74 is also provided and is equipped with a petcock or other quick release value indicated at 75 which may be opened to rapidly dissipate the suction in the system should that be desired at any time, for instance, just prior to opening of the closure 54 of the vacuum chamber in preparation for removing a suction bag.

Another branch 76 of the suction system extends to the bleed valve 77 which is adjustable by the nob 78 and this line also includes the normally closed solenoid valve 79 adapted to be opened and closed by the timer 47 having controls 48 and 49, as above described, for regulating the intermittent operation, both with respect to the length of the suction periods and also the intervals between the intermittent suction periods.

In this system for intermittent operation, the adjustable valve 77 may be used to establish and control the minimum suction level. In this way, in combination with the device 38a, both the maximum and minimum suction levels may be adjusted independently. When the timer 47 permits the valve 79 to close, then the suction level is established by the valve 38a, and when the timer operates to open the valve 79 the adjustable valve 77 will permit additional air to bleed into the system. The valve 77 may be adjusted so that even when the valve 79 is open, there will still remain a low level of suction in the system.

The provision of intermittent operation as just described provides an effective way of preventing backflow in the suction tube of the bag during the timed intervals of "rest", without employing the device for closing the suction tube, as shown in FIG. 3. This operation at timed alternate intervals of higher and lower suction is advantageous under certain conditions of use of the equipment, as it not only prevents backflow during the rest periods, but also provides for resting of the tissues and wound, and still further for dislodgement of any clot or material tending to accumulate and block the drainage system.

If it is desired to have no suction in the rest intervals, this may also be achieved by adjusting the valve 77 to its maximum opening, in which it is contemplated that sufficient air will bleed into the system through the branch connection 76 to completely dissipate the vacuum during the "rest" periods.

Still another branch 80 of the suction system is provided with two normally open solenoid operated valves 81 and 82 which are arranged in series, the line 80 ultimately terminating in a connector 32 and serving the same purpose as connector 32 above described in connection with the first embodiment. Thus, this connector is adapted to be coupled with the connector 28 of a wall vacuum outlet, a disconnectable tube 33 being provided for that purpose as in the earlier embodiments. This system provides for alternative operation of the equipment on the external source of suction instead of on the internal suction pump.

All of the elements in the system as described above in reference with FIG. 5, are adapted to be controlled by an electrical system diagrammatically indicated in FIG. 5 and here shown as including an ON/OFF push button switch 83 in the power line P. When the power switch 83 is in the ON position it provides for delivery of current to the three control switches indicated as push buttons 84, 85 and 86 (see also FIG. 6). When the push button 84 which is labeled PUMP is actuated, the motor 27 of the self-contained suction system is activated and in addition the solenoid valve 30 is opened, thereby providing for operation of the equipment on the self-contained suction source. At the same time, it will be seen that this circuit delivers current to the normally open solenoid valve 81 thereby closing that valve, so that the vacuum connection 80 is closed off. With the WALL STOP push button switch 86 operated, current is also delivered to the normally open solenoid valve 82 thereby closing that valve. The provision of the two normally open valves 81 and 82 thus provides for alternative operation either on the internal suction source or on the external suction source, and in addition this arrangement provides a safety factor which may be explained as follows.

Assuming the equipment is in operation on the self-contained suction source, it is only effective when electric power is available. If the electric power should fail (for instance by the opening of a circuit breaker or fuse), the failure of the power will, of course, result in termination of the operation of the self-contained suction source, but at the same time, the loss of current will result in opening of both of the normally open valves 81 and 82 and assuming the connection 33 has been made to the external source of suction, the operation of the equipment will automatically be diverted to and will continue operation on the external source of suction. On the other hand, even when power is available, the operation of the push button switches 84 and 86 will provide for selective operation either on the self-contained suction source or upon the external source, and when operating on the external source, the operation of the push button switch 86 may be used to either open or close the valve 82, which may from time to time be desired.

Since the solenoid valve 79 is a normally closed valve, the intermittent operation will only be operative when power is available. The intermittent functioning of the equipment may, of course, be controlled by the INT switch button 85 operated either to activate or deactivate the timer 47.

In considering the second embodiment, some features of the control panel as shown in FIG. 6 should be noted.

In the first place, it will be understood that the control panel may also be mounted on top of the vacuum chamber as indicated in FIG. 1. FIG. 6 shows a suitable disposition for the switches 83, 84, 85 and 86 and it may be observed in connection with those switches that they may each comprise a push button type of switch in which successive actuations of the push button results in successive connection and disconnection of the circuit. Desirably these push button switches contain signal lights and are color coded so that a glance at the control panel will inform the operator of the condition of the controls.

From FIG. 6, it will also be seen that the quick suction release petcock 75 is shown on the control panel, as is also the suction gauge 34 and the two adjustable control valves 38a and 78 which are provided respectively for regulating the high suction level and the low suction level, as described above. With regard to the low suction level, if desired, this adjustable valve may be interiorly disposed in the equipment so as not to be readily accessible to operating personnel and may even be a valve having a fixed setting, but for some purposes, it is advantageous to have this low suction level adjustment accessible on the control panel for use by the operating personnel.

It will also be noted that the illustration of the control panel in FIG. 6 does not indicate the adjustable controls 48 and 49 for the timer 47, and it is here contemplated that this timer and its controls may also be located interiorly of the equipment so as to require presetting, rather than normal adjustment by the operating personnel. On the other hand, if desired, the timer controls may be mounted on the control panel as is the case on the first embodiment described above and shown in FIG. 2.

Figures 7, 8, 9, 10, 11:
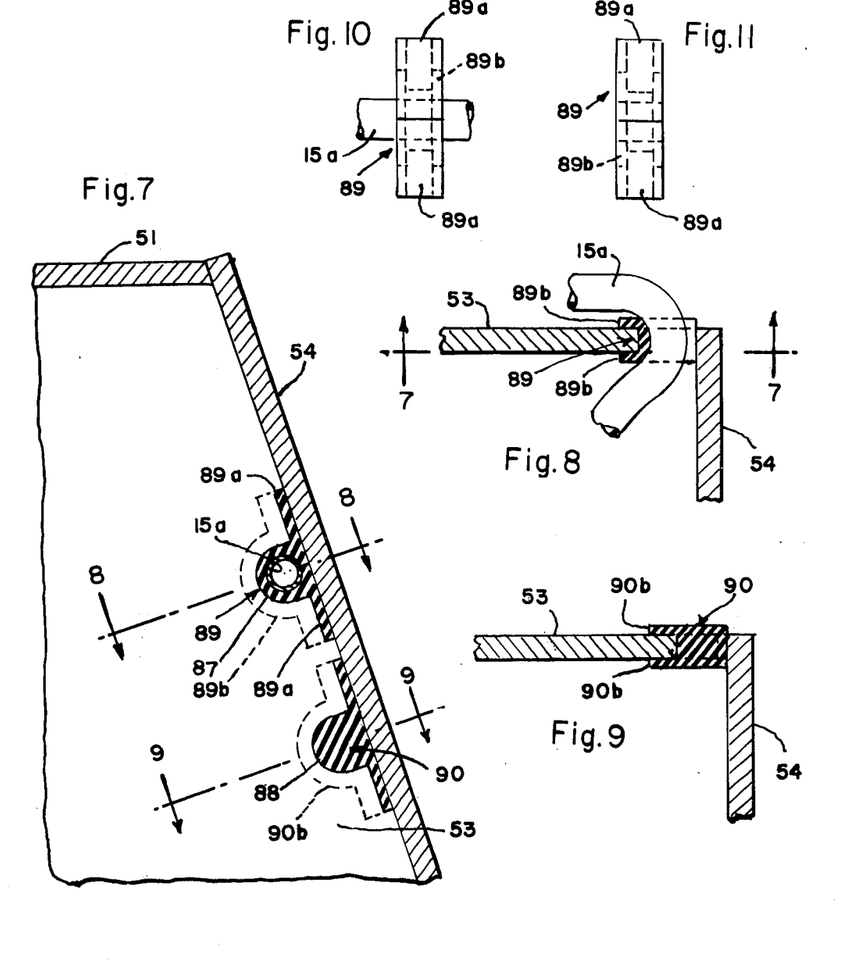
FIG. 7 is an enlarged view of certain details of construction of the embodiments of FIGS. 1 to 6 and particularly showing sealing means for use with the suction or intake tubes of the bags, this view being taken as indicated by the section line 7—7 on FIG. 8.
FIGS. 8 and 9 are fragmentary sectional views taken as indicated by the section lines 8—8 and 9—9 on FIG. 7.
FIGS. 10 and 11 are views illustrating certain details of tube sealing devices.

Turning now to the feature illustrated in FIGS. 7 to 11, it is first noted that a suction tube for a bag is indicated by the reference numeral 15a. From the enlarged fragmentary view of FIG. 7, it will be seen that the edge of the side wall 53 of the suction chamber is provided with two tube receiving notches or recesses 87 and 88. This has been done so that more than one bag each with a separate suction tube, may be mounted in the vacuum chamber, the equipment being capable of handling more than one bag, so that if required for some special purposes, liquids may be withdrawn separately from more than one source. Because of the vacuum or suction condition within the chamber, it is of course important to provide a substantially leak proof seal around the tube at the point where the tube passes through the wall of the chamber from the bag to the intake catheter. In the embodiment illustrated in FIGS. 7 to 11, each notch or recess such as indicated at 87 is desirably of larger size than the tube to be received, and a sealing device or adaptor is applied to the tube and seated in the notch 87. Advantageously the sealing device comprises an adaptor 89 formed of soft or resilient material, for instance, expanded or porus sponge type plastic such as polyvinyl chloride resin material. Alternatively, sponge or soft rubber may be used. As seen in FIG. 7, at each side of the adaptor 89 extended wings 89a are provided, and the notch in the side wall 53 desirably includes portions recessed to accommodate the wings 89a. Moreover the device 89 is also desirably provided with flanges indicated at 89b forming a channel structure embracing the side wall 53.

The sealing device 89 may completely surround the suction tube 15a, in which case it would be necessary to apply the sealing device to the tube by sliding it over one end of the tube and along the tube to the desired position. Alternatively, the sealing device may be slit at the side facing the closure 54, so that the device may be applied to the tube transversely.

It is contemplated that the sealing device snuggly fit the engaged surfaces of the side wall 53 of the vacuum chamber and also the adjacent flat surface of the closure door 54. Ordinarily, the suction tube itself is also formed of a soft or pliable plastic material, and by employing a sealing device of the kind described above, upon such a plastic tube, the sealing device may readily be proportioned so that the material thereof is placed under slight compression when the door 54 is closed, thereby assuring a leak proof joint where the tube passes out of the vacuum chamber.

The sealing device may constitute a separately handleable adaptor, as shown in FIG. 11, which may be applied to the suction tube at the time the bag and the tube are being inserted in the equipment for use. On the other hand, the sealing device may advantageously be adhesively secured or permanently bonded to a suction tube which is either integral with or which may be assembled with a suction bag. It is desirable to have the sealing device permanently fastened to the tube regardless of whether the tube is permanently fastened to the bag or comprises a separate component to be assembled with a bag. This has a special advantage which is explained as follows.

Various bags and associated suction tubes may be used in the equipment of the invention, the tubes being of different diameters. To insure a tight seal with tubes of different diameters, it is important that the sealing device have different dimensions corresponding to the individual dimensions of the tube being used. If the sealing device comprises a separate adaptor, there would necessarily have to be sealing devices of different sizes maintained in stock in order to have adaptors available for tubes of different sizes. However, if a properly proportioned sealing device is permanently fastened to each suction tube, errors in assembly are avoided. In all cases, of course, the external dimensions of the sealing devices are appropriate to the size of the notch in the edge of the chamber wall 53. Thus, by providing a sealing device permanently fastened or assembled with each tube, whether or not the tube is permanently assembled with a bag, a snug seal is assured, and therefore maintenance of the desired suction condition is also assured.

In the case of the presence of a notch such as indicated at 88 in FIG. 7 which at times is not being used for a suction tube, that notch may be closed by means of a "blank" adaptor as indicated at 90, this adaptor having flanges 90b as indicated to embrace the edge of the side wall 53 and to provide for complete enclosure of that notch when it is not being used for a suction tube.

Instead of the sealing arrangements illustrated in FIGS. 7 to 11, the alternative embodiment of FIGS. 14 to 18 may be employed and, indeed, the embodiment of FIGS. 14 to 18 has a number of important and distinctive features and advantages as will further appear.

In FIG. 14 the vacuum compartment is defined by various walls, such as the upright side walls indicated at 53, and the wall structure is provided with a doorway with which the door 54 cooperates in order to provide an openable vacuum compartment for receiving the suction bag 16 which may be suspended in the vacuum compartment by means of hooks 64.

In this embodiment, one of the side walls 53 has an edge notch 91 of V-shape adapted to receive the sealing device, which, in this embodiment, is of triangular configuration. The sealing device comprises a triangular body portion 92 and a triangular flange portion 93 lying at one side of the body portion 92 and projecting beyond all three sides of the body portion. The sealing device is centrally apertured to receive the suction tube 15 of the bag 16.

The dimensions of the body portion 92 are adapted to snuggly fit the notch 91 in the side wall 53, and to provide for snug engagement with the overlying portion of the door 54 when the door is closed.

As shown, the flange portion 93 is adapted to engage the outer surface of the side wall 53 of the vacuum chamber, adjacent to the notch 91.

As illustrated, it will be seen that the edge of the chamber wall adjacent to the doorway has an edge notch of angular shape representing at least two flat sides of a regular polygon, the notch opening representing still another side of the polygon. The sealing device itself has the shape of said regular polygon and this configuration of the notch and of the sealing device is of advantage because it permits insertion of the seal in the notch in any one of a number of angular positions. The use of an equilateral triangular configuration for both the notch and the sealing device provides the advantage just mentioned of employing a notch and seal having the shape of a regular polygon, but the triangular configuration has additional advantages including the fact that the triangular shape provides an automatic centering action when the seal is inserted in the notch, and this is true regardless of which of the three corners of the triangle is brought into registry with the notch during insertion. The resulting ease of insertion of the seal into the notch is a factor of considerable importance in order to facilitate and expedite the changing of bags.

The triangular configuration is also especially advantageous for other reasons, including the fact that the triangular shape most readily lends itself to providing the desired snug fit between the seal and the notch of the side wall of the compartment as well as between the seal and the door.

From the manufacturing standpoint also, the triangular shape of the seal and the notch is important. In fabricating the side wall and forming the notch therein, it is relatively easy to provide an accurate V-shaped notch, and in the formation of the seal device, the triangular shape is one which is readily provided, particularly in a molding operation, as is contemplated.

The configuration of the sealing device, having the flange part 93 overlying the wall surface adjacent to the notch is also an important feature, because, when the door is closed and the vacuum is established in the compartment, the flange part 93 is drawn against the surface of the side wall of the compartment adjacent to the notch, thereby providing a "self-tighting" action and further enhancing the tightness of the seal around the suction tube 15.

As above indicated, it is contemplated that both the bag 16 and the tube 15 are desirably formed of flexible plastic material, and the flexibility of these components is also of importance, because it further facilitates the self-tighting action produced by the establishment of the vacuum in the chamber when the door is closed. The flexibility of the parts with which the seal is associated is also of importance from the standpoint of insertion of the sealing device into the notch, because with the flexible tube and bag, the sealing device may readily be turned or shifted in position during insertion, in order to properly seat the sealing device in the notch.

The sealing device is advantageously molded of plastic material, for instance polyvinyl chloride or neoprene or it may be formed of vulcanized rubber. The material is advantageously somewhat yielding and resilient and the size of the sealing device is desirably slightly larger than the notch, so that when the door is closed it will tend to force the material of the sealing device into the notch and thereby provide tight interengagement.

The sealing device desirably has a central passage or bore to receive the tube 15 which bore is slightly larger in diameter than the outside diameter of the tube. The bore, however, is provided with a bead such as indicated at 95 in FIG. 16 projecting inwardly and having an inside diameter slightly less than the outside diameter of the tube in order to engage the external surface of the suction tube. This bead will serve to provide the seal between the sealing device itself and the tube and will also facilitate insertion of the tube through the sealing device as compared with a configuration in which the entire length of the bore tightly engages the outside surface of the tube.

Figures 17, 18:
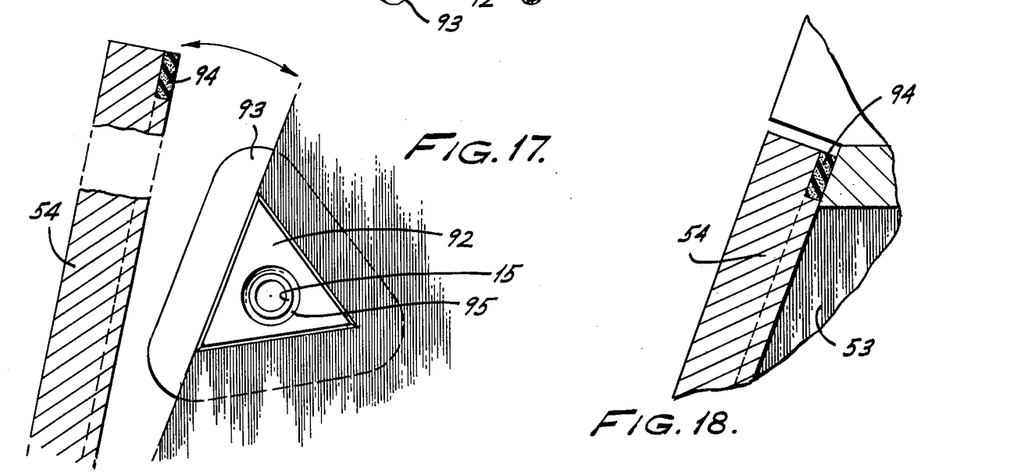
FIG. 17 is an enlarged fragmentary side elevational view of portions of the wall structure of the vacuum compartment, with the tube sealing device associated therewith, and of a section of the door in open position, the sectional part of this view being taken as indicated by the section line 17-18 on FIG. 14.
FIG. 18 is a fragmentary sectional view of a portion of the door illustrated in section as indicated by the section line 17-18 on FIG. 14, but with the door in its closed position.

Although the seal device may be employed in association with a rigid door having a hard sealing surface, it is preferred that the door be provided with a sealing gasket which is extended not only in the region on the tube sealing device, but also throughout the entire perimeter of the door. As seen in FIGS. 17 and 18, the door is advantageously provided with a cut-out around the edge thereof in order to receive the resilient gasket 94 positioned to engage the surfaces of the wall structure of the vacuum compartment around the doorway or opening provided. The presence of this gasket provides an effective seal under the action of the vacuum within the compartment, the external atmospheric pressure serving to tightly engage the gasket with the surfaces surrounding the doorway and also with the outwardly presented surface of the tube sealing device.

There is still another advantage resulting from the location of the sealing gasket 94 in an edge cut-out extended around the perimeter of the door. Thus, when the door is closed and the vacuum established in the compartment, the external atmospheric pressure acting against the edge of the gasket would tend to shift the gasket inwardly, but this is prevented by virtue of the accommodation of the gasket in the edge cut-out which provides a shoulder around the perimeter of the door resisting inward displacement of the gasket.

As with the embodiment described earlier, the arrangement of FIGS. 14 to 18 also contemplates, that a plurality of notches may be provided in the wall of the compartment in order to accommodate more than one bag. In addition, it is also here contemplated that if more than one notch is employed, or if a notch is not used, it may be closed by a "blank" sealing device.

Still further, as with the embodiment described above, it is contemplated that sealing devices may be provided for cooperation with suction tubes of certain sizes.

As above indicated, the bag, suction tube and sealing device may comprise a disposable unit, but alternatively, as with the embodiment of the sealing device described above in connection with FIGS. 7 to 11, the sealing device and tube may comprise a disposable unit independently of the bag, which, of course, may also be disposable. For certain purposes, it may be advantage to provide for separate disposal of bags on the one hand and tubes with sealing devices on the other hand. As seen in FIG. 14, for this purpose, the tube 15 may be separable from the nipple 96 provided on the bag.

In all embodiments, the use of the vacuum system to produce the suction in the suction bag is advantageous from a number of standpoints including the fact that this system facilitates the employment of disposable suction bag and suction tube components. It will be observed that no part of the disposable components need be introduced into any mechanical pump device. Moreover, the system of the present invention is capable of establishing and maintaining a given suction condition immediately from outset of operation, and this condition will be maintained at the selected suction or pressure level without variation, regardless of fluctuations of the quantity of liquid in the suction tube or in the suction bag.

The equipment is simple, inexpensive and reliable and presents virtually no hazards from the standpoint of contamination of the non-disposable portions of the apparatus.

The embodiments of FIGS. 1–4 and of FIGS. 5–6 are also very flexible and adaptable to use under a variety of conditions and in a variety of positions, since the equipment may readily be wheeled from place to place. The arrangement of the vacuum chamber in the embodiments of FIGS. 1–4, 5–6 and 14–18 with the pivotally mounted door or closure 54 also provides maximum convenience in introducing and removing the suction bags.

I claim:

1. Medical/surgical suction equipment comprising a vacuum chamber with a vacuum connection, the chamber having an opening with a notched wall at an edge of the opening, a door for closing said opening having a flat surface overlapping the wall notch, the door cooperating with the chamber wall to define a closed but openable vacuum compartment, a disposable and replaceable suction bag in the vacuum compartment for receiving body liquids, a disposable suction tube connected with the bag, at least a portion of the tube being flexible and extending through said notch to a point outside of the compartment for intake of body liquids, and a disposable vacuum sealing device surrounding and mounted on the tube, the sealing device having a flat surface for engagement with the flat surface of the door, having a portion configured to engage the notch of the chamber wall and further having a flange lying in a plane transverse to the tube and adapted to overlap the surface of the notched wall outside of the vacuum compartment, the bag, tube and sealing device being handleable as a disposable unit and being unitarily removable when the door is open.

2. Medical/surgical suction equipment comprising a vacuum chamber with a vacuum connection, the chamber having an opening with a chamber wall at an edge thereof formed with an edge notch of V-shape representing two sides of an equilateral triangle, a door for closing said opening having a flat surface overlapping the wall notch and having an edge lying in the plane of the outside surface of said chamber wall, the door cooperating with the chamber wall to define a closed but openable vacuum compartment, a disposable and replaceable suction bag in the vacuum compartment for receiving body liquids, a disposable suction tube connected with the bag, at least a portion of the tube being flexible and extending through said notch to a point outside of the compartment for intake of body liquids, and a disposable vacuum sealing device surrounding and mounted on the tube, the sealing device having a portion in the shape of an equilateral triangle substantially conforming in size with said equilateral triangle represented by said V-shaped notch and thereby provide for presentation of a flat side thereof for engagement with the flat surface of the door regardless of which corner of the triangular portion of the sealing device is inserted into the notch, the sealing device also having a flange lying in a plane transverse to the tube and projecting beyond all three sides of the triangular portion to overlap the surface of the notched wall outside of the vacuum compartment and also the edge of the door lying in the plane of said outside surface regardless of which corner of the triangular portion of the sealing device is inserted into the notch, the bag, tube and sealing device being handleable as a disposable unit and being unitarily removable when the door is open.

3. Medical/surgical suction equipment comprising a vacuum chamber with a vacuum connection, the chamber having an opening with a chamber wall at an edge thereof formed with an edge notch of angular shape representing at least two flat sides of a regular polygon and with the notch opening representing one flat side of said regular polygon, a door for closing said opening having a flat surface overlapping the wall notch and having an edge lying in the plane of the outside surface of said chamber wall, the door cooperating with the chamber wall to define a closed but open-able vacuum compartment, a disposable and replaceable suction bag in the vacuum compartment for receiving body liquids, a disposable suction tube connected with the bag, at least a portion of the tube being flexible and extending through said notch to a point outside of the compartment for intake of body liquids, and a disposable vacuum sealing device surrounding and mounted on the tube, the sealing device having a portion in the shape of a regular polygon sub-stantially conforming in shape and size with said regular polygon represented by said angular notch and thereby provide for presentation of a flat side thereof in the notch opening for engagement with the flat surface of the door regardless of which portion of the polygonal portion of the sealing device is inserted into the notch, the sealing device also having a flange lying in a plane transverse to the tube and projecting beyond all sides of the polygonal portion to overlap the surface of the notched wall outside of the vacuum compartment and also the edge of the door lying in the plane of said outside surface regardless of which portion of the polygonal portion of the sealing device is inserted into the notch, the bag, tube and sealing device being handleable as a disposable unit and being unitarily removable when the door is open.

4. For use in combination with medical/surgical suction equipment having a vacuum chamber with a vacuum connection and further with an opening with a notched wall at an edge of the opening and with a displaceable closure member for said opening having a flat surface overlapping the wall notch and cooperating to define a closed but openable vacuum compartment for receiving a disposable suction bag for body liquids, a disposable suction tube for the bag at least a portion of which is flexible and extends through said notch to a point outside of the compartment, and a sealing device surrounding and mounted on said flexible portion of the tube, the sealing device having a flat surface for engagement with the flat surface of the displaceable closure member, having a portion configured to engage the notch of the chamber wall and having a flange lying in a plane transverse to the tube and adapted to be positioned adjacent the surface of the notched wall outside of the vacuum compartment.

5. Equipment as defined in claim 4 and further in which a disposable suction bag is connected with the disposable suction tube to provide for unitary removal and replacement of a connected bag, tube and sealing device.

6. Equipment for withdrawing body liquids comprising a vacuum chamber with a vacuum line connection, the chamber having a first wall structure with a doorway formed therein, a door comprising an openable wall structure cooperating with the doorway in the first wall structure to define a closed but openable vacuum compartment, a replaceable suction bag in said compartment having an opening for interconnecting the interior of the bag with said compartment and further having a liquid inlet tube with the tube wall connected with the wall of the bag, the vacuum line connection for the chamber being attached to the chamber wall structure independently of the bag and its liquid inlet tube, the wall structures of the chamber and door having portions cooperating to form a channel through which the bag inlet tube may be extended, a vacuum sealing device surrounding the tube and shaped to fit said channel, the channel providing for unitary separation of the bag, tube and sealing device from the wall structures of the chamber and door when the door is open, and thus for unitary removal and insertion of connected bags and tubes with tube sealing devices, independently of the vacuum line connection for the chamber.

7. Equipment as defined in claim 6 in which one of said cooperating wall structures of the chamber and door is provided with a notch to provide said channel for the liquid inlet tube of the bag and in which the other of said wall structures has a flat surface overlapping the tube notch, the sealing device surrounding the tube being configured to fit said notch and having a flat surface presented for interengagement with the flat surface of said other wall structure.

8. Equipment as defined in claim 6 in which said first wall structure has a notch to provide said channel for the liquid inlet tube of the bag and in which the door has a flat surface overlapping the tube notch, a yielding sealing gasket on said flat surface of the door, the sealing device surrounding the tube being configured to fit said notch and having a flat surface presented for interengagement with said gasket, and the door having a shoulder positioned inboard of said gasket to resist inward displacement of the gasket under the influence of atmospheric pressure when the chamber is evacuated.

9. Equipment for withdrawing body liquids comprising a vacuum chamber, the chamber having a first wall structure with a doorway formed therein, a door comprising an openable wall structure cooperating with the doorway in the first wall structure to define a closed but openable vacuum compartment, a replaceable suction bag in said compartment having a liquid inlet tube with the tube wall connected with the wall of the bag, the wall structures of the chamber and door having portions cooperating to form a channel through which the bag inlet tube may be extended, a vacuum sealing device surrounding the tube and shaped to fit said channel, the portion of the sealing device adjacent the outer surface of the wall structure of the chamber being of larger cross sectional area than the cross sectional area of at least a portion of the channel thereby providing for tightening of the seal under the influence of atmospheric pressure when the chamber is evacuated, the channel providing for unitary separation of the bag, tube and sealing device from the wall structures of the chamber and door when the door is open, and thus for unitary removal and insertion of connected bags and tubes with tube sealing devices.

* * * * *